(12) United States Patent
Correa et al.

(10) Patent No.: US 10,258,958 B2
(45) Date of Patent: Apr. 16, 2019

(54) PHOTOCHEMICAL HYDROGENATION OF HEAVY FRACTIONS OF HYDROCARBON STREAMS

(71) Applicants: PETROLEO BRASILEIRO S.A.—PETROBRAS, Rio de Janeiro, RJ (BR); UNIVERSIDADE FEDERAL DO RIO DE JANEIRO—RJ, Rio de Janeiro-RJ (BR)

(72) Inventors: Rodrigo Jose Correa, Rio de Janeiro (BR); Felipe Pereira Fleming, Rio de Janeiro (BR)

(73) Assignees: PETROLEO BRASILEIRO S.A.—PETROBRAS, Rio de Janeiro (BR); UNIVERSIDADE FEDERAL DO RIO DE JANEIRO, Rio de Janeiro (BR)

(*) Notice: Subject to any disclaimer, the term of this patent is extended or adjusted under 35 U.S.C. 154(b) by 330 days.

(21) Appl. No.: 15/347,275

(22) Filed: Nov. 9, 2016

(65) Prior Publication Data
US 2017/0128907 A1 May 11, 2017

(30) Foreign Application Priority Data
Nov. 10, 2015 (BR) .............. 10 2015 028294

(51) Int. Cl.
*C07C 5/10* (2006.01)
*B01J 19/12* (2006.01)
*C07D 487/22* (2006.01)

(52) U.S. Cl.
CPC .............. *B01J 19/123* (2013.01); *C07C 5/10* (2013.01); *C07D 487/22* (2013.01); *B01J 2219/0871* (2013.01); *B01J 2219/0877* (2013.01); *B01J 2219/1203* (2013.01)

(58) Field of Classification Search
CPC .............. B01J 19/123; B01J 2219/0877; B01J 2219/0871; B01J 2219/1203; C07D 487/22; C07C 5/10
See application file for complete search history.

(56) References Cited

U.S. PATENT DOCUMENTS

| | | | | |
|---|---|---|---|---|
| 3,663,393 A | * | 5/1972 | Latourette | .............. B01J 19/081 204/157.6 |
| 4,168,218 A | * | 9/1979 | Dedinas | .................. B41M 5/30 204/157.9 |
| 5,824,214 A | | 10/1998 | Paul et al. | |
| 2010/0275509 A1 | * | 11/2010 | Sakuma | .............. B01J 35/0006 44/438 |
| 2013/0277273 A1 | | 10/2013 | Mazyar | |

* cited by examiner

*Primary Examiner* — Nicholas A Smith
*Assistant Examiner* — Colleen M Raphael
(74) *Attorney, Agent, or Firm* — Sughrue Mion, PLLC

(57) ABSTRACT

The present invention describes a photochemical hydrogenation process for heavy fractions of hydrocarbon streams where the aromatic and polyaromatic compounds present in that fraction selectively react in the presence of an alkoxide, when subjected to electromagnetic irradiation.

8 Claims, 4 Drawing Sheets

PHOTOCHEMICAL HYDROGENATION OF HEAVY FRACTIONS OF HYDROCARBON STREAMS

CROSS REFERENCE TO RELATED APPLICATIONS

This application claims priority based on Brazilian Patent Application No. 10 2015 028294-0, filed Nov. 10, 2015, the contents of which are incorporated herein by reference in their entirety.

INVENTION FIELD

The present invention provides a photochemical hydrogenation process for heavy fractions of hydrocarbon streams, which are converted into lighter fractions, to improve the physicochemical properties, especially the viscosity and density of such currents.

BASIS OF THE INVENTION

Oil is the second-largest source of energy in the world and, with the rise of global discoveries of heavy oil (12 to 22.3° API, as defined by the ANP [Agência Nacional do Petróleo, Gás Natural e Biocombustíveis (Brazilian National Agency of Petroleum, Natural Gas and Biofuels)]) and ultra-heavy oil (≤12° API, as defined by the ANP), production, transportation and refining of these oils have become the subject of studies and research.

The value of oil and the costs of production and refining are associated with the physicochemical properties thereof. The less viscous and less dense it is, the greater the added value of crude oil and the lower the production-chain costs.

Some aromatic compounds present in crude oil can lead to an increase in density and viscosity, especially heavier fractions such as resins and asphaltenes. Asphaltenes constitute the fraction of heavier and polar crude-oil compounds, having polycondensate aromatic structures in general, and containing different functional groups, molecular structures and relatively large molecular mass distribution.

In addition to providing increased oil density and viscosity, the tendency of precipitation of asphaltenes when obtaining crude oils can lead to severe consequences such as reduced oil flow or even blocking of the processing lines during production, transportation and refining of oils, and can poison catalysts in the refining processes.

One option for minimizing the deleterious effects of asphaltenes is the hydrogenation thereof, as hydrogenation reduces the attractive forces between the "core" of the aromatic hydrocarbons of asphaltene molecules, as well as reduces the incidence of clustering or precipitation of molecules in suspension, which ultimately leads to reducing its viscosity.

Thus, numerous studies have been carried out on this subject. Document US 2013/0277273, for example, describes the hydrogenation of aromatic compounds present in crude oil in the presence of a catalyst and hydrogen. The catalyst used is a supported catalyst comprising a metal from Group IB, Group IVB, Group VB, Group VIB, Group VIIB, or Group VIII of the periodic table, including but not limited to: chromium, iron, manganese, molybdenum, tungsten, vanadium, silver, gold, nickel, palladium, platinum, rhodium, ruthenium, or a mixture thereof.

Meanwhile, document U.S. Pat. No. 5,824,214 describes the treatment of a heavy crude oil containing at least 1% water by weight by sonic energy at a low frequency of 400 Hz to 10 kHz, directly on the bottom of a petroleum production well, in the presence of a metal hydrogenation catalyst. In this process, hydrogen is formed from water as defined by the reaction:

In another embodiment of the invention, if the heavy crude oil does not have sufficient water content, hydrogen can be formed in situ through contact of heavy crude oil in the bottom of the well with a chemical compound comprising ammonia, hydrazine and formic acid, which, in the presence of a metal hydrogenation catalyst and sonic energy, leads to the formation of hydrogen by causing the hydrogenation reaction, and a resulting reduction in viscosity.

However, there is no literature, description or suggestion of a process for hydrogenation of aromatic compounds, in particular of asphaltenes, present in hydrocarbon streams to reduce the viscosity and density of such currents without the need to use a catalyst, and this process is described and claimed below.

SUMMARY OF THE INVENTION

In a broad manner, the present invention is for a process for the hydrogenation of aromatic heavy fractions, containing one or more aromatic rings, including asphaltenes from hydrocarbon streams by means of a photochemical process where these aromatic compounds of heavy fractions are hydrogenated in the presence of an alkoxide, when subjected to electromagnetic irradiation.

DETAILED DESCRIPTION OF THE INVENTION

In general, the invention is based on the reactivity of aromatic compounds present in heavy fractions of hydrocarbon streams with an alkoxide when subjected to electromagnetic irradiation.

In the case of asphaltenes, as they have aromatic polycondensate structures that exhibit characteristic absorption spectra, they are able to absorb electromagnetic radiation in a wide range of wavelengths. Depending on the degree of aromatic ring condensation, the molecule absorbs radiation in the UV (ultraviolet) wavelength range up to near infrared (NIR), going through the entire visible spectrum (VIS).

The process comprises the use of electromagnetic radiation, which can be either in the ultraviolet spectrum (UV—wavelength of 100 to 400 nm) or the visible spectrum (wavelength of 400 to 780 nm), preferably between 450 and 700 nm. In this excited state of aromatic molecules, it is possible to extract an electron followed by a hydrogen radical from the alkoxide radical, which can be obtained from the reaction of a base with a hydroxy organic compound.

Figure 1:
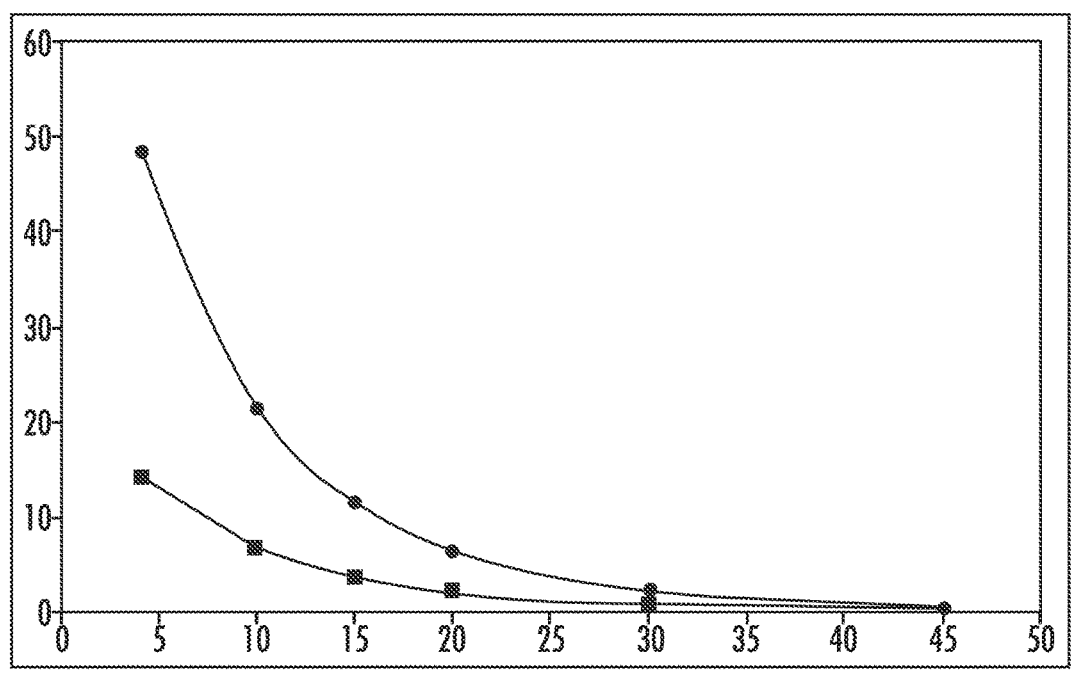
FIG. 1 illustrates the reduction in viscosity in centipoise in an experiment conducted in the presence of sodium isopropoxide and 80% by mass of oil, as a function of temperature.
Figure 2:
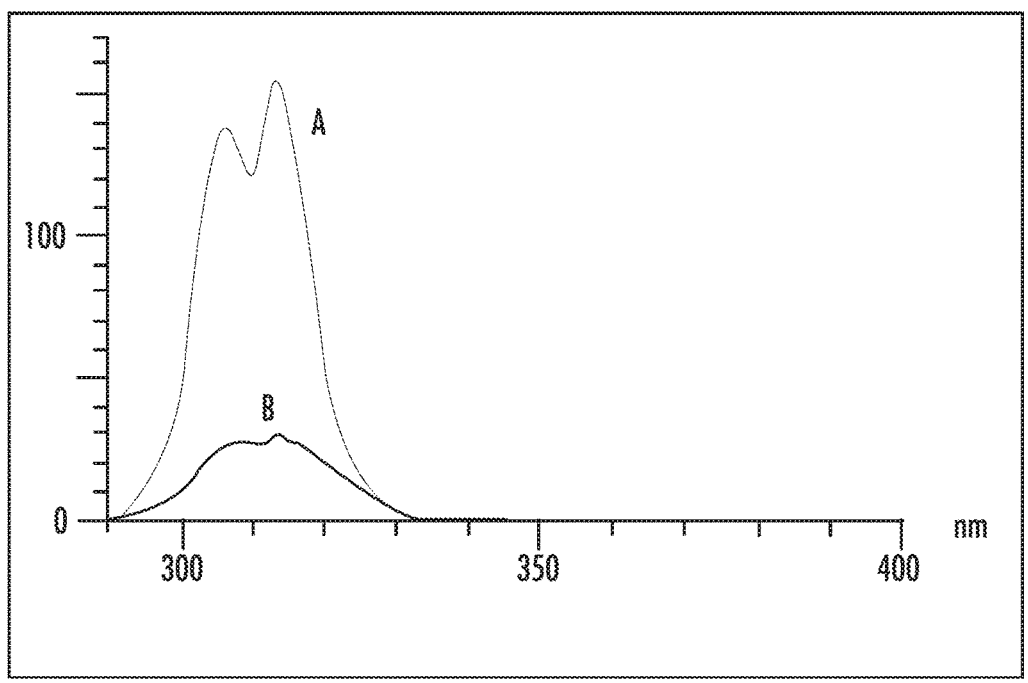
FIG. 2 illustrates the synchronous fluorescence spectrum of a naphthalene sample in 2-propanol in an alkaline medium (200 mM NaOH), and curve A is for the sample when not irradiated and curve B is for the sample after UV-VIS irradiation.
Figure 3:
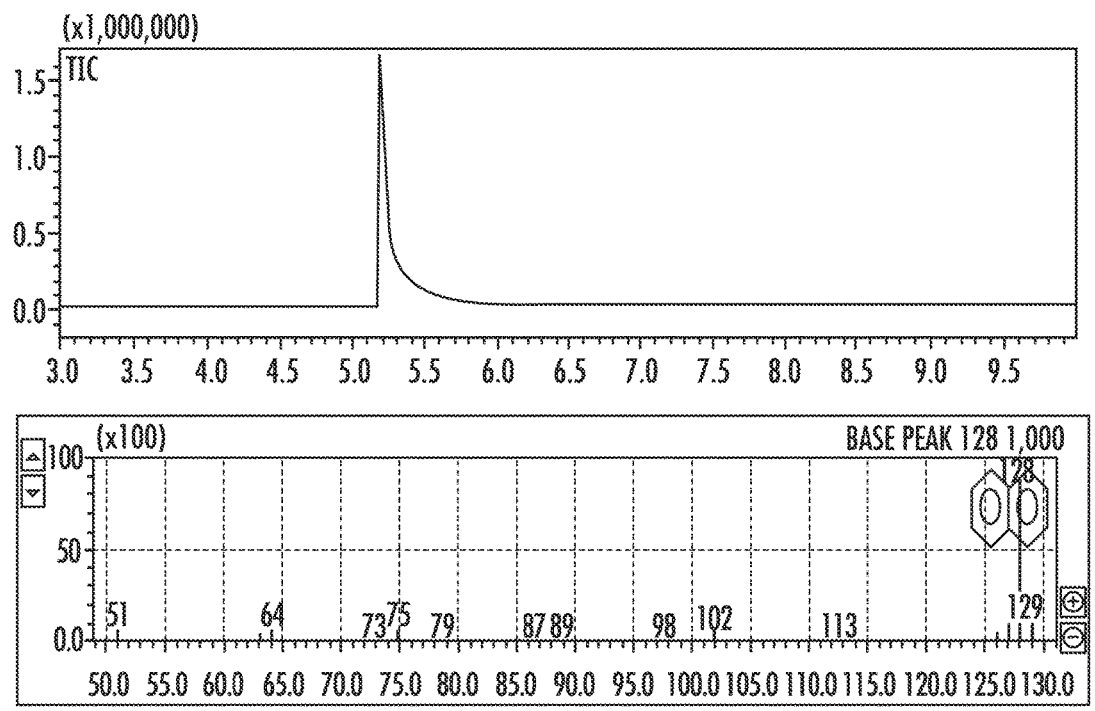
FIG. 3 illustrates the results of GCMS analysis on a naphthalene sample, not irradiated in 2-propanol in an alkaline medium (200 mM NaOH).
Figure 4:
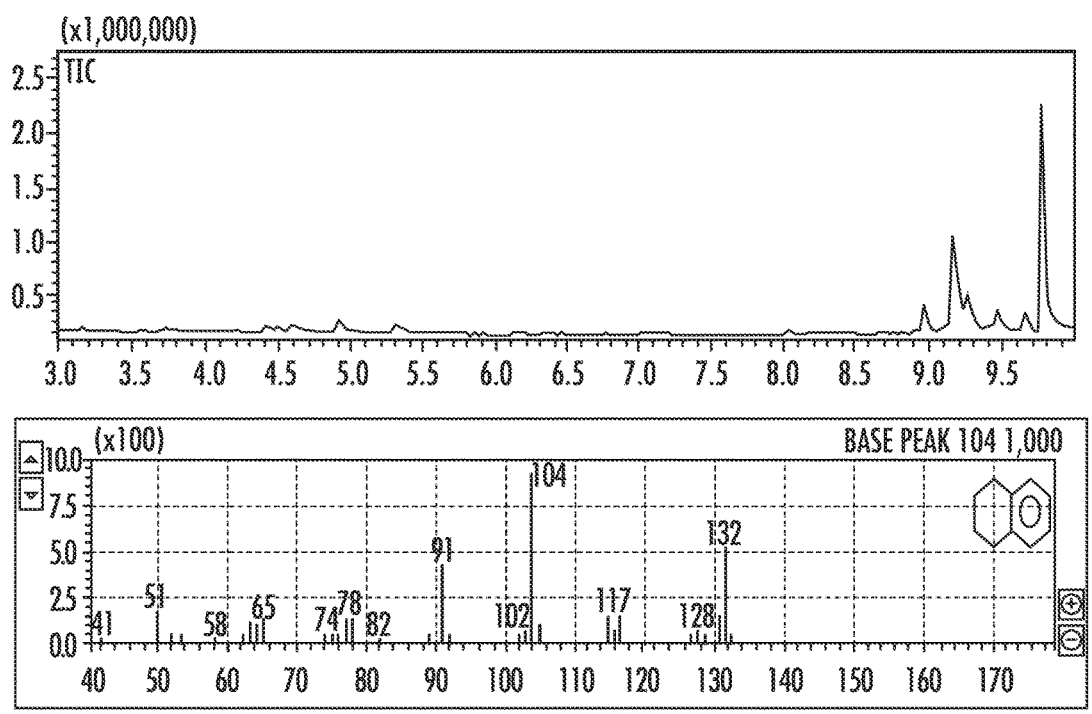
FIG. 4 illustrates the results of GCMS analysis on a naphthalene sample, in 2-propanol in an alkaline medium (200 mM NaOH), irradiated for eight hours.
Figure 5:
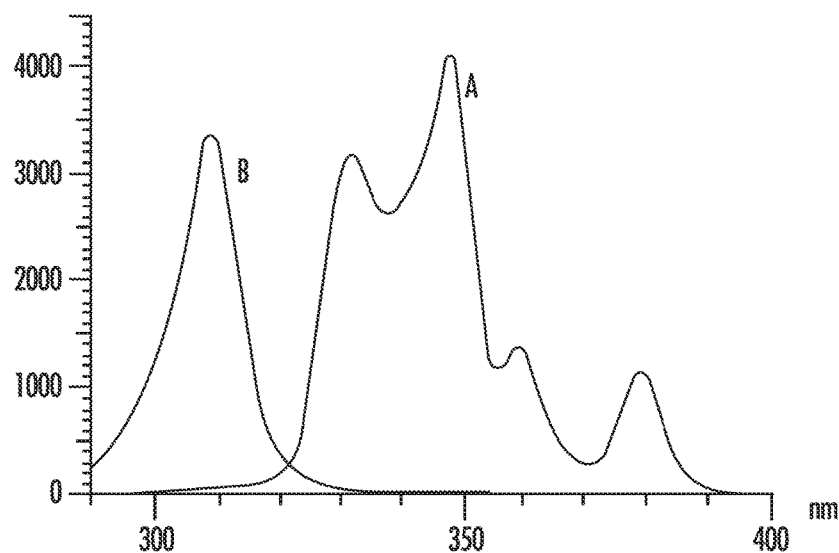
FIG. 5 illustrates the synchronous fluorescence spectrum of a sample of phenanthrene in 2-propanol, in an alkaline medium (200 mM NaOH), and curve A is for the sample when not irradiated and curve B is for the sample after UV-VIS irradiation.
Figure 6:
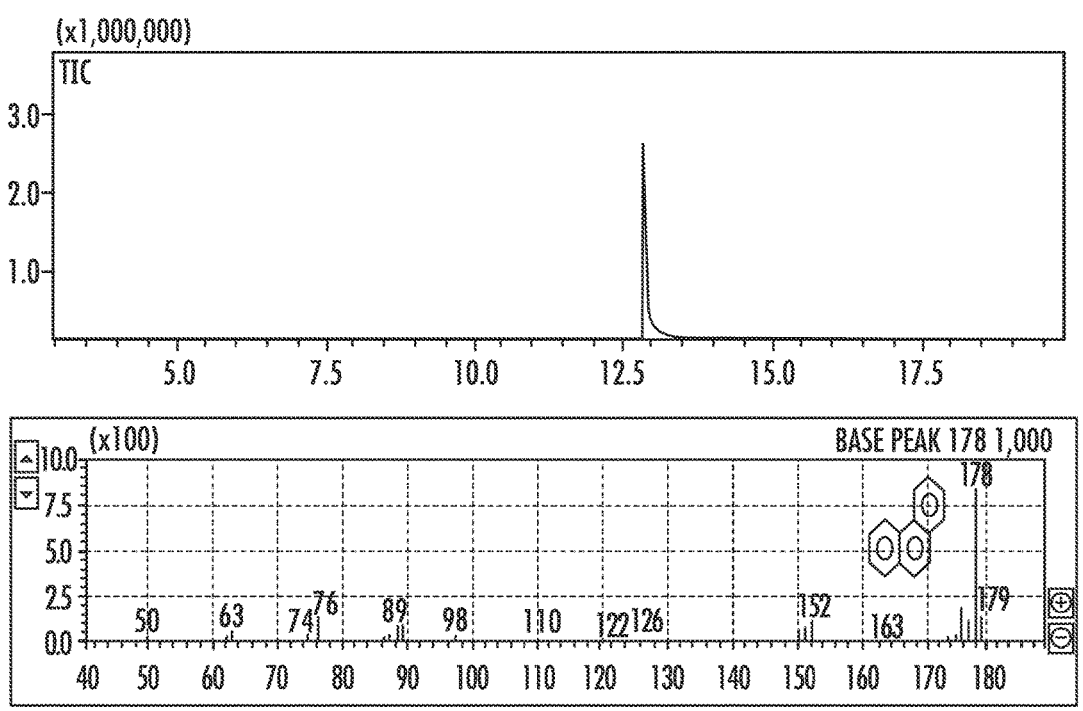
FIG. 6 illustrates the results of GCMS analysis of a sample of phenanthrene in 2-propanol, in an alkaline medium (200 mM NaOH), not irradiated.
Figure 7:
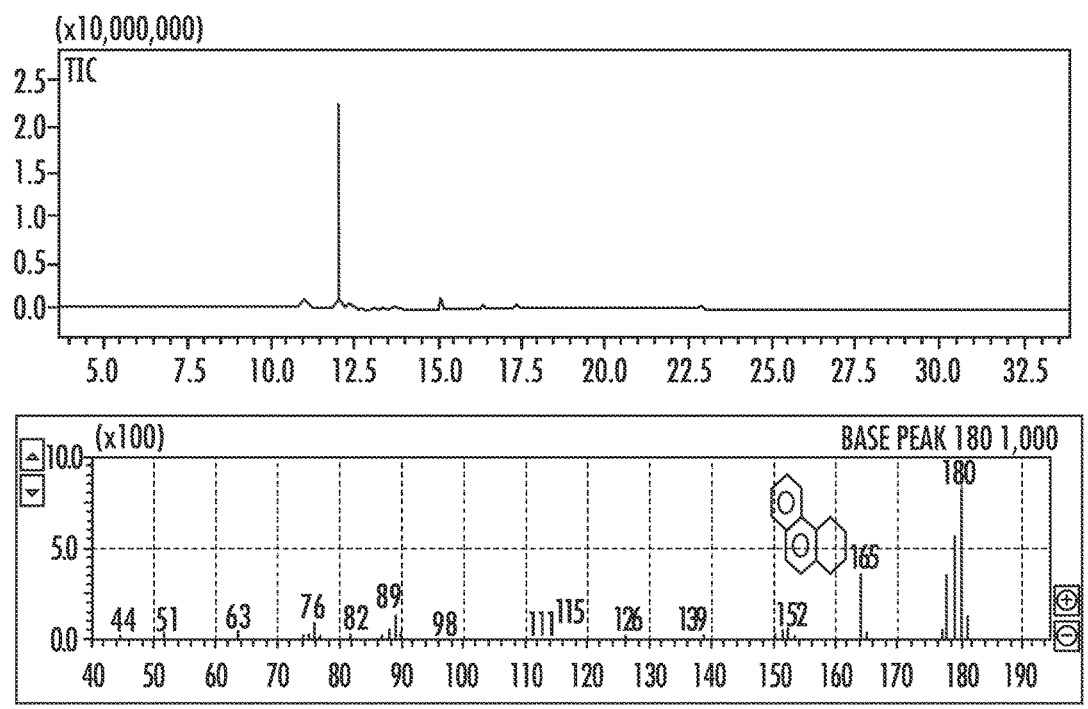
FIG. 7 illustrates the results of GCMS analysis of a sample of phenanthrene in 2-propanol, in an alkaline medium (200 mM NaOH), irradiated for eight hours.
Figure 8:
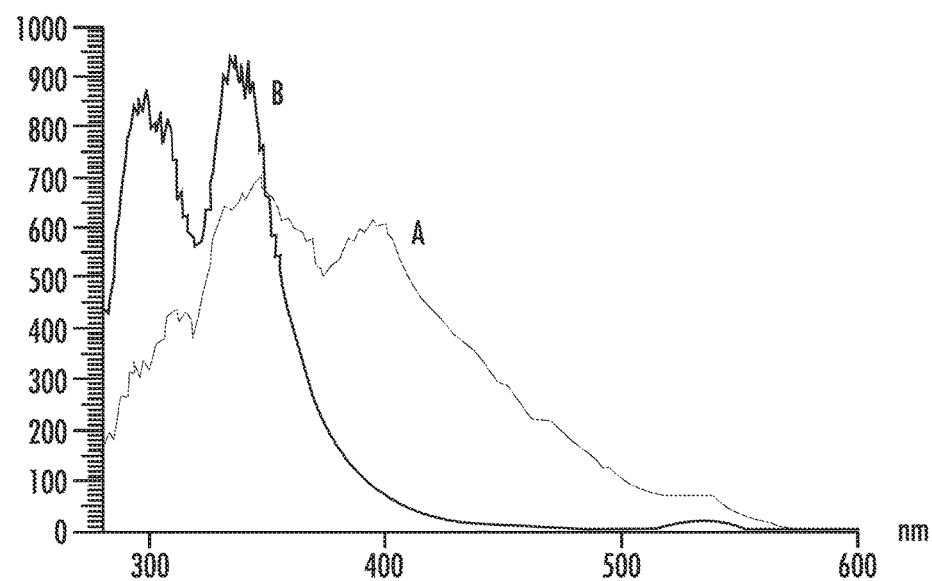
FIG. 8 illustrates the synchronous fluorescence spectrum of a sample of petroleum in 2-propanol, in an alkaline medium (200 mM NaOH), and curve A is for a sample when not irradiated and curve B is for the sample after UV-VIS irradiation.

Thus, in the presence of a hydroxy organic compound and a base, aromatic molecules are selectively reduced in the unsaturations present in the aromatic ring. Usually, the reaction is partial, but this becomes more selective as a function of the applied radiation. Thus, the process is selective for heavy oil fractions and especially for aromatic compounds such as asphaltenes, without interfering in the light fractions, as can be observed in the synchronous fluorescence spectra and analysis of the results by GCMS obtained for samples of naphthalene, phenanthrene, and an oil sample, illustrated in FIGS. 2 to 8.

Therefore, the present invention is for a process of hydrogenation of heavy fractions by reacting hydrocarbon streams with an alkoxide under radiation action in the UV-VIS range, obtaining a hydrocarbon stream with low density and viscosity, said process including the following steps:

a) Provide a load for the process consisting of a hydrocarbon stream, comprising a heavy fraction of hydrocarbons, containing aromatic compounds with one or more condensed rings in a concentration higher than 0.1% by mass;

b) Add at least one alkoxide to the load in a ratio of 1 to 1 molar in relation to the hydrocarbons that are to be reduced, at a temperature in the range of 20 to 60° C. and at atmospheric pressure, with stirring, to obtain a load/alkoxide homogeneous mixture;

c) Subject the mixture obtained to electromagnetic radiation of a wavelength in the UV-VIS range, for a period of five minutes to 48 hours, to obtain a processed stream with density and viscosity less than the original load.

Preferably, the process load is a hydrocarbon stream containing non-negligible levels of asphaltenes, and these compounds are significant in the viscosity of the load. Such streams may have concentrations of their heavy fraction greater than 0.1% by mass, chains containing an asphaltene fraction in the range of 1 to 80% by mass being preferred.

The heavy fractions are basically comprised of aromatic compounds, in particular polyaromatic compounds of high molecular weight that have auto-associative capacity and significantly influence the density and viscosity of a load.

In more detail, the photochemical hydrogenation process of heavy fractions of hydrocarbon streams of the present invention involves selective reaction of an alkoxide with an aromatic compound in the excited state. This mechanism involves four steps:

formation of the excited state of the aromatic compound due to irradiation of the sample with electromagnetic radiation of a wavelength in the UV-VIS range;

this excited state is oxidizing and extracts an electron from the alkoxide;

the anion radical of the aromatic compound extracts a hydrogen radical from the alkoxide radical, generating a ketone; and the aromatic anion extracts a middle proton.

The reaction products are a compound carbonylated from alcohol and a cyclic unsaturated compound from the aromatic compound.

The selection of the aromatic compound to be hydrogenated is done by the wavelength of the applicable electromagnetic radiation (light). The longer the wavelength, the higher the degree of condensation of the ring comprised of aromatic compounds present in the hydrocarbon stream to react.

In the case of directly using the alkoxide, this, in principle, is any conjugate base of any organic compound containing a chain of one to six carbon atoms and having one or more hydroxyls, such as, for example: ethoxide, isopropoxide, methoxide, glyceroxide, etc. The alkoxide should be present in a stoichiometric amount to reduce the desired type in the stream.

Moreover, the alkoxide may be the result of the reaction between an alcohol and a base. The alcohol to be used may, in principle, contain from one to six carbon atoms, being mono- or polyhydroxy, such as ethanol, isopropanol, and preferably glycerol (or glycerine), or mixtures thereof.

In this process, the base serves only to increase the concentration of alkoxide anions in the reaction medium, but may also be any base capable of removing a proton from the hydroxy compound used or mixtures thereof. These include: sodium hydroxide, potassium hydroxide, metal sodium, sodium formate, calcium formate, calcium oxide, or mixtures thereof.

The quantities of base and of alcohol, when used, necessary in the process, are stoichiometric for conversion of the content of aromatic compounds to be hydrogenated in each oil and/or fractions thereof, in the molar ratio 1:1:1.

The examples below correspond to laboratory scale experiments without limiting the scope of the process, described in detail here.

EXAMPLES

Example 1

The tests described below were carried out in a photochemical reactor, where an aromatic compound was dissolved in dichloromethane at different concentrations, ranging from 10 to 1000 mg/L. To irradiate the samples, a medium-pressure mercury lamp and 450 W were used. This lamp emits mainly UV between 250 and 450 nm. Each sample was irradiated for 12 hours with constant stirring, in the absence and presence of oxygen in the reaction medium.

The following were used as aromatic compounds: naphthalene, phenanthrene, pyrene, benzo-pyrene, coronene, porphyrins and asphaltene samples obtained from different Brazilian oils.

For the reaction with the aromatic compounds, an alkoxide obtained by the reaction of a base with an alcohol was used.

Pyrene was tested against the alcohols: methanol, ethanol, isopropanol and glycerol. The other aromatics were tested only against ethanol. The alcohol was used at concentrations of 10 mg/L to 10%.

With regard to the bases, pyrene was tested against the bases: sodium hydroxide, calcium hydroxide and calcium formate. The other aromatics were tested only against sodium hydroxide. Pyrene was also tested against sodium ethoxide, without adding more alcohol.

The process was accompanied by UV-VIS and fluorescence spectra of the reaction mixture. The UV-VIS spectrum was recorded between 200 and 500 nm. The fluorescence spectrum was recorded by the synchronous method, with emission of 250 to 500 nm and distance of 20 nm between excitation and emission, migration of the UV-VIS spectra to shorter wavelengths and a reduction in the intensity of the fluorescence spectrum having been observed, indicating a reduction in the condensation of aromatic rings present in the medium.

Example 2

The invention is based on the reactivity of aromatic compounds in the presence of an alkoxide, obtained by reacting a base and an alcohol, when subjected to irradiation by ultraviolet or visible light from a reactor with a mercury vapor 450-watt lamp. This lamp mainly emits UV between 250 and 450 nm. The samples were irradiated for 12 hours with constant stirring in the absence and presence of oxygen in the reaction medium. Phenanthrene and naphthalene were partially hydrogenated when irradiated by UV-VIS in the presence of an NaOH solution in 2-propanol in a stoichiometric ratio.

The aromatic compounds studied were pyrene, benzo-pyrenes, coronene, porphyrins and asphaltene samples from oils with different API degrees from 8 to 30° API. The series of alcohols used in the process consisted of methanol, ethanol, 2-propanol, butanol, pentanol, hexanol and glycerol. The bases used were sodium hydroxide, potassium hydroxide, calcium formate. The process schema is shown in the tables below:

| Alcohols | Sample Naphthalene | | |
|---|---|---|---|
| Methanol | 200 mM NaOH | 200 mM KOH | 200 mM Calcium Formate |
| Ethanol | 200 mM NaOH | 200 mM KOH | 200 mM Calcium Formate |
| 2-propanol | 200 mM NaOH | 200 mM KOH | 200 mM Calcium Formate |
| Butanol | 200 mM NaOH | 200 mM KOH | 200 mM Calcium Formate |
| pentanol | 200 mM NaOH | 200 mM KOH | 200 mM Calcium Formate |
| glycerol | 200 mM NaOH | 200 mM KOH | 200 mM Calcium Formate |

| Alcohols | Sample Phenanthrene | | |
|---|---|---|---|
| Methanol | 200 mM NaOH | 200 mM KOH | 200 mM Calcium Formate |
| Ethanol | 200 mM NaOH | 200 mM KOH | 200 mM Calcium Formate |
| 2-propanol | 200 mM NaOH | 200 mM KOH | 200 mM Calcium Formate |
| Butanol | 200 mM NaOH | 200 mM KOH | 200 mM Calcium Formate |
| pentanol | 200 mM NaOH | 200 mM KOH | 200 mM Calcium Formate |
| glycerol | 200 mM NaOH | 200 mM KOH | 200 mM Calcium Formate |

| Alcohols | Sample Pyrene | | |
|---|---|---|---|
| Methanol | 200 mM NaOH | 200 mM KOH | 200 mM Calcium Formate |
| Ethanol | 200 mM NaOH | 200 mM KOH | 200 mM Calcium Formate |
| 2-propanol | 200 mM NaOH | 200 mM KOH | 200 mM Calcium Formate |
| Butanol | 200 mM NaOH | 200 mM KOH | 200 mM Calcium Formate |
| pentanol | 200 mM NaOH | 200 mM KOH | 200 mM Calcium Formate |
| glycerol | 200 mM NaOH | 200 mM KOH | 200 mM Calcium Formate |

| Alcohols | Sample Benzo-pyrene | | |
|---|---|---|---|
| Methanol | 200 mM NaOH | 200 mM KOH | 200 mM Calcium Formate |
| Ethanol | 200 mM NaOH | 200 mM KOH | 200 mM Calcium Formate |
| 2-propanol | 200 mM NaOH | 200 mM KOH | 200 mM Calcium Formate |
| Butanol | 200 mM NaOH | 200 mM KOH | 200 mM Calcium Formate |
| pentanol | 200 mM NaOH | 200 mM KOH | 200 mM Calcium Formate |
| glycerol | 200 mM NaOH | 200 mM KOH | 200 mM Calcium Formate |

| Alcohols | Sample Coronene | | |
|---|---|---|---|
| Methanol | 200 mM NaOH | 200 mM KOH | 200 mM Calcium Formate |
| Ethanol | 200 mM NaOH | 200 mM KOH | 200 mM Calcium Formate |
| 2-propanol | 200 mM NaOH | 200 mM KOH | 200 mM Calcium Formate |
| Butanol | 200 mM NaOH | 200 mM KOH | 200 mM Calcium Formate |
| pentanol | 200 mM NaOH | 200 mM KOH | 200 mM Calcium Formate |
| glycerol | 200 mM NaOH | 200 mM KOH | 200 mM Calcium Formate |

| Alcohols | Sample Tetraphenylporphyrin | | |
|---|---|---|---|
| Methanol | 200 mM NaOH | 200 mM KOH | 200 mM Calcium Formate |
| Ethanol | 200 mM NaOH | 200 mM KOH | 200 mM Calcium Formate |
| 2-propanol | 200 mM NaOH | 200 mM KOH | 200 mM Calcium Formate |
| Butanol | 200 mM NaOH | 200 mM KOH | 200 mM Calcium Formate |
| pentanol | 200 mM NaOH | 200 mM KOH | 200 mM Calcium Formate |
| glycerol | 200 mM NaOH | 200 mM KOH | 200 mM Calcium Formate |

| Alcohols | Sample A Asphaltene - API grade >20 oil | | |
|---|---|---|---|
| Methanol | 200 mM NaOH | 200 mM KOH | 200 mM Calcium Formate |
| Ethanol | 200 mM NaOH | 200 mM KOH | 200 mM Calcium Formate |
| 2-propanol | 200 mM NaOH | 200 mM KOH | 200 mM Calcium Formate |
| Butanol | 200 mM NaOH | 200 mM KOH | 200 mM Calcium Formate |
| pentanol | 200 mM NaOH | 200 mM KOH | 200 mM Calcium Formate |
| glycerol | 200 mM NaOH | 200 mM KOH | 200 mM Calcium Formate |

| Alcohols | Sample B Asphaltene - API grade <20 oil | | |
|---|---|---|---|
| Methanol | 200 mM NaOH | 200 mM KOH | 200 mM Calcium Formate |
| Ethanol | 200 mM NaOH | 200 mM KOH | 200 mM Calcium Formate |
| 2-propanol | 200 mM NaOH | 200 mM KOH | 200 mM Calcium Formate |
| Butanol | 200 mM NaOH | 200 mM KOH | 200 mM Calcium Formate |
| pentanol | 200 mM NaOH | 200 mM KOH | 200 mM Calcium Formate |
| glycerol | 200 mM NaOH | 200 mM KOH | 200 mM Calcium Formate |

Hydrogenation of aromatic samples was found in all series of alcohols used, as well as with the three types of bases tested. The 2-propanol, together with the sodium hydroxide, yielded the most satisfactory results, namely a higher level of hydrogenation compared to other substrates in the study.

The invention claimed is:

1. Photochemical hydrogenation process for heavy fractions of hydrocarbon streams, characterized in that it comprises the reaction of aromatic compounds, present in the heavy fraction of hydrocarbon streams, with an alkoxide, in the presence of electromagnetic irradiation in the UV-VIS range, and temperatures in the range of 20 to 60° C. and at atmospheric pressure.

2. Photochemical hydrogenation process for heavy fractions of hydrocarbon streams, according to claim 1, characterized in that it comprises the following steps:
   a) Provide a load for the process consisting of a hydrocarbon stream, comprising a heavy fraction of hydrocarbons, containing aromatic compounds with one or more condensed rings in a concentration higher than 0.1% by mass;
   b) Add at least one alkoxide to the load in a ratio of 1 to 1 molar in relation to the hydrocarbons that are to be reduced, at a temperature in the range of 20 to 60° C. and at atmospheric pressure, with stirring, to obtain a load/alkoxide homogeneous mixture;
   c) Subject the mixture obtained to electromagnetic radiation of a wavelength in the UV-VIS range, for a period of five minutes to 48 hours, to obtain a processed stream with density and viscosity less than the original load.

3. Photochemical hydrogenation process for heavy fractions of hydrocarbon streams, according to claim 1, characterized in that the aromatic compounds are chosen from: phenanthrene, naphthalene, pyrene, benzo-pyrenes, coronene, asphaltenes, porphyrins and their derivatives, or mixtures thereof.

4. Photochemical hydrogenation process for heavy fractions of hydrocarbon streams, according to claim 1, characterized in that the alkoxide is obtained by reacting a conjugate base with an alcohol, containing a chain with one to six carbon atoms.

5. Photochemical hydrogenation process for heavy fractions of hydrocarbon streams, according to claim 4, characterized in that the alcohol is monohydric.

6. Photochemical hydrogenation process for heavy fractions of hydrocarbon streams, according to claim 5, characterized in that the alcohol is polyhydric.

7. Photochemical hydrogenation process for heavy oil fractions, according to claim 5, characterized in that the alcohol is chosen from: ethanol, 2-propanol, glycerol, or a mixture thereof.

8. Photochemical hydrogenation process for heavy fractions of hydrocarbon streams, according to claim 5, characterized in that the conjugate base is chosen from: sodium hydroxide, potassium hydroxide, metal sodium, sodium formate, calcium formate, calcium oxide, or mixtures thereof.

* * * * *